: US Patent [19] [11] Patent Number: 5,341,693
Banu [45] Date of Patent: Aug. 30, 1994

[54] DOUBLE WALL SAMPLER

[75] Inventor: John Banu, Plantation, Fla.

[73] Assignee: Ocean Test Equipment, Inc., Fort Lauderdale, Fla.

[21] Appl. No.: 4,414

[22] Filed: Jan. 14, 1993

[51] Int. Cl.⁵ ............................................. G01N 1/12
[52] U.S. Cl. .................... 73/864.67; 73/864.63
[58] Field of Search ........... 73/864.63, 864.66, 864.67; 138/103, 107–110, 114, 118, 137, 147; 383/59, 60, 67, 78, 80, 81, 100, 118, 904

[56] References Cited

U.S. PATENT DOCUMENTS

| | | | |
|---|---|---|---|
| 2,751,787 | 6/1956 | Porter | 73/864.63 |
| 3,242,740 | 3/1966 | Niskin | 73/864.67 X |
| 3,365,953 | 1/1968 | Gold et al. | 73/864.67 X |
| 3,426,745 | 2/1969 | Farr | 73/864.63 |
| 3,489,012 | 1/1970 | Niskin | 73/863.31 |
| 3,815,422 | 6/1974 | Niskin | 73/864.67 |
| 4,037,477 | 7/1977 | Niskin | 73/864.67 X |
| 4,091,676 | 5/1978 | Niskin | 73/864.67 |
| 4,302,974 | 12/1981 | Niskin | 73/864.62 |
| 4,347,751 | 9/1982 | Niskin et al. | 73/864.63 |
| 4,593,357 | 6/1986 | Niskin | 73/864.67 |
| 4,744,625 | 5/1988 | Niskin | 73/864.66 |
| 4,852,413 | 8/1989 | Niskin | 73/864.67 |
| 5,094,113 | 3/1992 | Wood | 73/864.67 |
| 5,113,711 | 5/1992 | Davloor et al. | 73/864.63 |

FOREIGN PATENT DOCUMENTS

| | | | |
|---|---|---|---|
| 188405 | 11/1966 | U.S.S.R. | 73/864.67 |
| 626383 | 9/1978 | U.S.S.R. | 73/864.67 |
| 800783 | 2/1981 | U.S.S.R. | 73/864.63 |
| 807119 | 2/1981 | U.S.S.R. | 73/864.63 |
| 851167 | 7/1981 | U.S.S.R. | 73/864.63 |
| 596600 | 1/1948 | United Kingdom | 73/864.63 |

OTHER PUBLICATIONS

*Oceanoloy (USA)* vol. 16, pub Sep. 1976, pp. 94–95 "A Hermetically Sealed Combination Sampler and Degasser", by V. I. Avilov.

Primary Examiner—Thomas P. Noland
Attorney, Agent, or Firm—Herbert L. Lerner; Laurence A. Greenberg

[57] ABSTRACT

A water sampler of the general type has a substantially rigid body with two end portions with openings for receiving a water sample. Two end plugs close off the openings, for entrapping a water sample inside the body. The improvement comprises a flexible liner inside the rigid body. The flexible liner receives the water sample such that any direct contact between the water sample and the rigid body is avoided.

5 Claims, 8 Drawing Sheets

FIG. 1

PRIOR ART

DOUBLE WALL SAMPLER

BACKGROUND OF THE INVENTION

1. Field of the Invention

The present invention relates to samplers, particularly to water samplers used to collect samples of water from the ocean and from lakes or rivers.

2. Summary of the Prior Art

The best-known sampler of this general type is a sampler known among those skilled in the art as the "Niskin Bottle", as described in U.S. Pat. Nos. 3,489,012 and 3,815,422. In fact, the instantly disclosed invention is an improvement over the Niskin Bottle and the full disclosure of the two patents is herewith incorporated by reference.

A number of other patents are pertinent in this respect, namely the following U.S. Pat. Nos.:

| | | |
|---|---|---|
| 3,242,740 | 3,425,664 | 3,986,635 |
| 4,037,477 | 4,091,676 | 4,106,751 |
| 4,302,974 | 4,347,751 | 4,593,570 |
| 4,744,256 | 4,852,413 | 5,094,113. |

In briefly reviewing the Niskin Bottle, as quite aptly described also in U.S. Pat. No. 5,094,113, it includes a generally cylindrical tubular body with two lids on either sides which are biased closed by a resilient rubber band clamped between the two lids. The tubular body is formed of hard PVC material. After the sample is taken, the same is retained in the sampler for a certain period of time before it is analyzed. Any contamination of the sample, which would lead to false analysis results, must thereby be strictly avoided. Analytic instruments have become increasingly sophisticated, so that only slight alterations and contamination of the sample often have an adverse effect on the testing outcome. When the sample remains in the bottle for a time period in the order of one or a few hours, for instance, false results in terms of concentration in the water sample results. In some instances it is also necessary to avoid contact of the water sample with air when the water sample is extracted from the sampler.

In a more specific example, the sampler is immersed in sea water at a given depth, often as much as three miles, or even more. The sample is then encapsulated by closing the end caps. It takes a certain amount of time to bring the sampler back to the surface and prepare the same for analysis. During that time period, the rigid PVC body of the prior art sampler can contaminate the water sample by reacting with the water and the impurities contained therein. Furthermore, when the liquid is purged from the sampler, air is allowed to enter the device through the air vent, in order to equilibrate the pressure and to facilitate the purge. This causes the air to come in contact with the water sample and gases entrapped in the water sample to be released. All of this results in an incorrect reading of the actual amounts and concentration of elements in the water sample. Finally, the rigid PVC body is a relatively good conductor with regard to temperature exchange between the ambient atmosphere and the water sample contained therein. Accordingly, the sample will rather quickly assume the temperature of its environment while it is prepared for analysis.

SUMMARY OF THE INVENTION

It is accordingly an object of the invention to provide a double walled sampler, which overcomes the hereinaforementioned disadvantages of the heretofore-known devices of this general type and which, to a much greater degree than the prior art devices, avoids contamination of the sample, even if the same is left in the sampler for a long period of time.

With the foregoing and other objects in view there is provided, in accordance with the invention, in a water sampler of the type having a substantially rigid body with two end portions with openings for receiving a water sample, two end plugs for closing the openings, and means for closing the end plugs by remote action so as to entrap a water sample in the substantially rigid body, an improvement which comprises: a flexible liner body disposed within the rigid body for receiving the water sample and for preventing direct contact between the water sample and the rigid body.

In accordance with an added feature of the invention, the flexible liner body is formed of a material which is essentially inert relative to at least water and sodium chloride. In particular, that material may be polyethylene, in accordance with another feature of the invention.

In accordance with a further feature of the invention, the sampler includes upper collar means disposed between the rigid body and an upper end plug, lower collar means disposed between the rigid body and a lower end plug, the flexible liner means being sealingly attached to the upper and lower collar means, the flexible liner means together with the upper and lower collar means and the upper and lower end plugs defining a sealed container for a water sample.

In accordance with yet another feature of the invention, the water sampler includes valve means disposed in the lower collar means for selectively purging water sample from the sealed container.

In accordance with a concomitant feature of the invention, the upper collar means are disposed between the upper end plug and the rigid body in such a manner as to allow air or water to enter a space defined between the flexible liner means and the rigid body.

The sampler according to the invention has a rigid body portion, usually tubular, and a pair of opposed end plugs secured to the two ends of the body. When the end plugs are closed, the water sample is entrapped in the sampler. Attached to the two ends of the body is a leak proof flexible body, usually tubular, made of polyethylene or any other material which is known to be inert relative to water and/or the elements and compounds expected to be found in the sample to be taken. In other words, the person of skill in the art will be able, without undue experimentation, to choose a proper material for a proper environment. Materials such as polyethylene are known to be highly inert relative to all of the compounds expected to be found in a water sample.

The flexible body is secured in place by two collars. The collars are placed in the body so as to allow water or air to be able to enter the space in between the flexible body and the wall of the hard body, such that the flexible body can easily collapse when water sample is withdrawn therefrom.

A crucial improvement over the prior art is thus found in the fact that the sample, when being purged, is not exposed to air entering through the top air vent.

Furthermore, the fluid sample is placed in a generally inert environment.

Another improvement over prior art samplers is found in the relatively simpler attachment mechanisms to a rosette.

Furthermore, windows are provided in the hard PVC body, so as to allow direct visual examination of the sample.

Other features which are considered as characteristic for the invention are set forth in the appended claims.

Although the invention is illustrated and described herein as embodied in a double-walled sampler, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
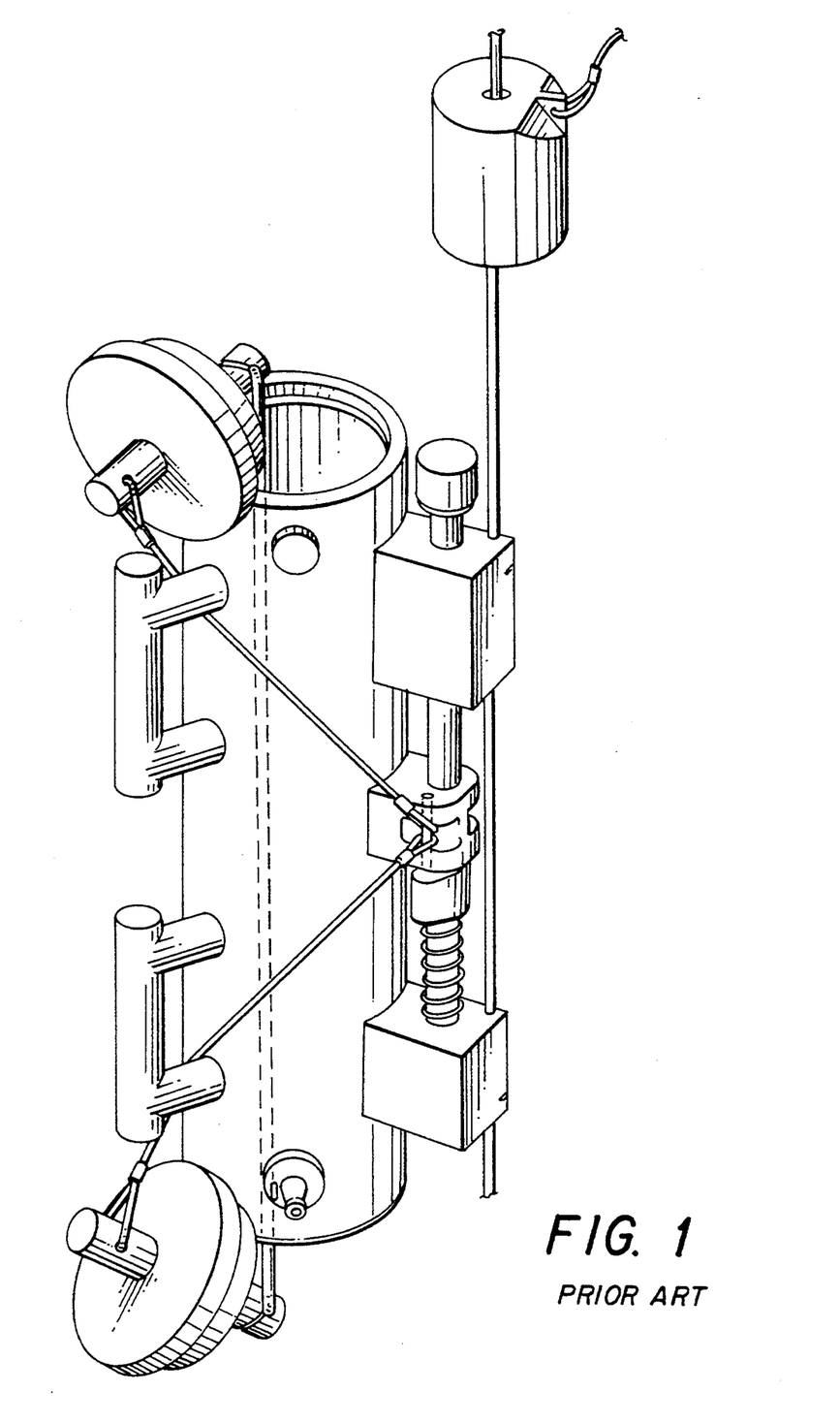
FIG. 1 is a perspective view of a prior art sampler.

As mentioned above, the sampler shown in FIG. 1 is a so-called Niskin Bottle. Since the corresponding patent is herein incorporated by reference and since the person of skill in this art is familiar with that and similar samplers, the same will not be described herein in any detail.

Figure 2:
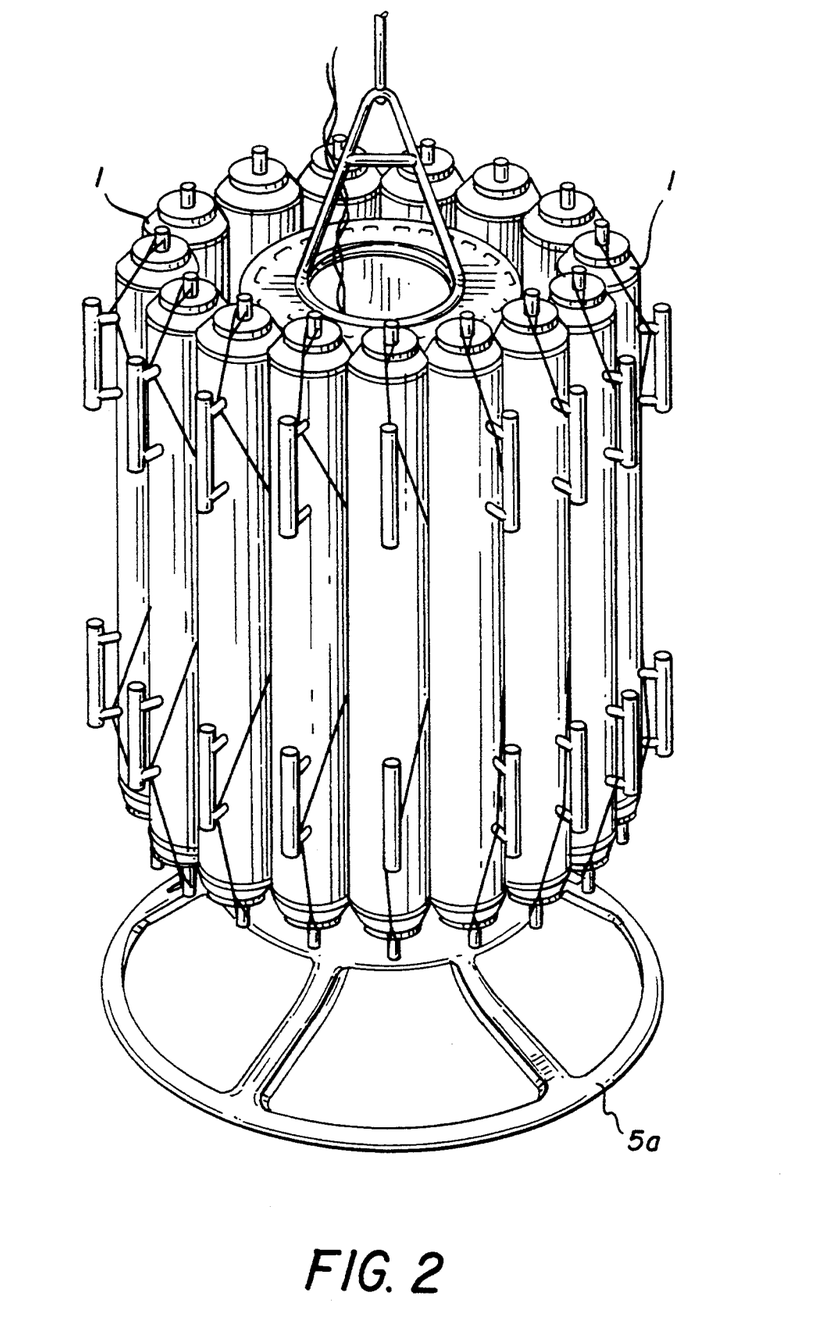
FIG. 2 is a perspective view of an arrangement of a plurality of samplers disposed on a rosette.
Figure 3:
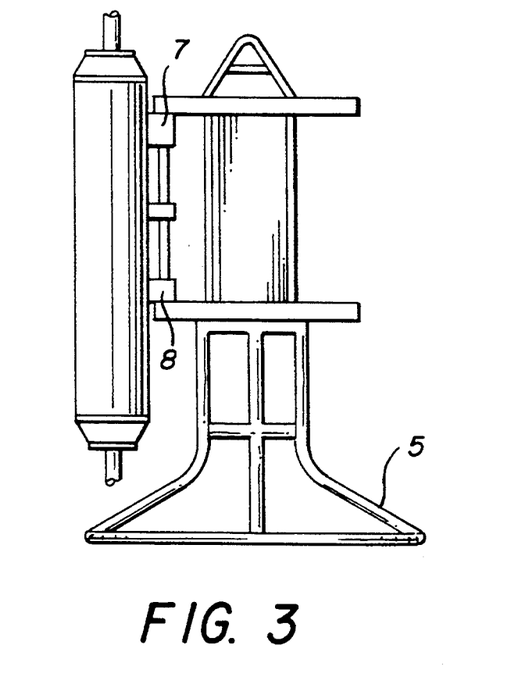
FIG. 3 is a side-elevational view of a single sampler attached to a rosette.

Similar arguments apply to FIGS. 2 and 3, in which the collars between the cylindrical body and the end plugs are indicated. The conical portions illustrating the collars will be described in the following in the context of the invention.

Figure 4:
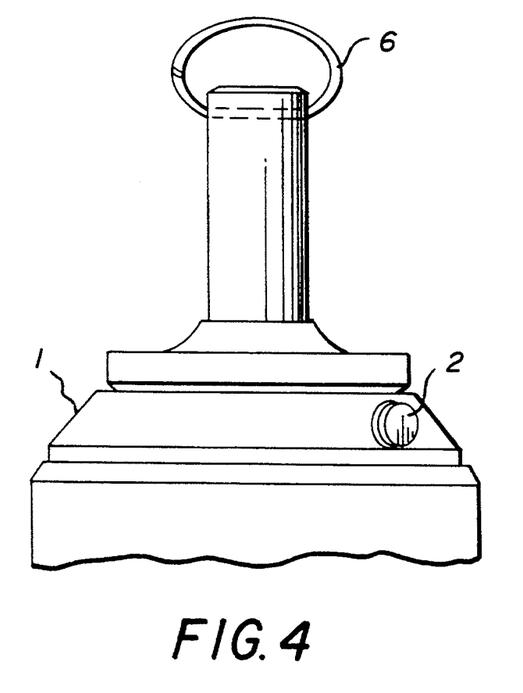
FIG. 4 is a side-elevational, partial view of a sampler showing an air vent according to the invention.

Referring now to the figures of the drawing in detail and first, particularly, to FIG. 4 thereof, there is seen an upper portion of a sampler with an air vent 2 disposed on the conical portion 1. The air vent 2 is no longer necessary in the context of this invention, because an inside body is provided which collapses when sample is purged. However, when it is desired to purge very quickly and to force sample out of the sampler, a pressurized inert gas source is connected to the air vent 2 and the sample is in effect blown out of the sampler.

Figure 5:
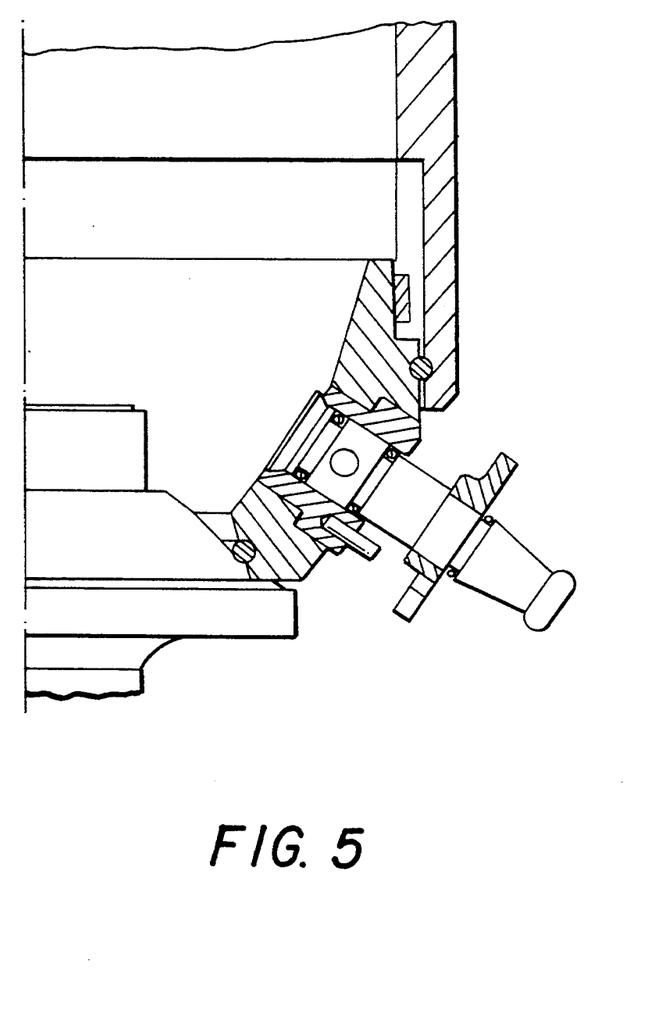
FIG. 5 is a cross-sectional view through a bottom portion of the sampler showing a sample dispensing valve assembly.

A cross section of the conical portion 1 with a sample dispensing valve 3 disposed therein is illustrated in FIG. 5. The valve 3 in itself is known from the prior art and will not be explained in detail. It is only important, in this context, that the valve communicates with the interior of the double-walled sampler, i.e. with the inside space of the flexible, collapsible liner, which is disposed inside the hard PVC pipe. The most inert of the currently envisioned materials for the liner is polyethylene. Other materials are possible as well and will be chosen by the person of skill in this art without undue experimentation.

Figure 6:
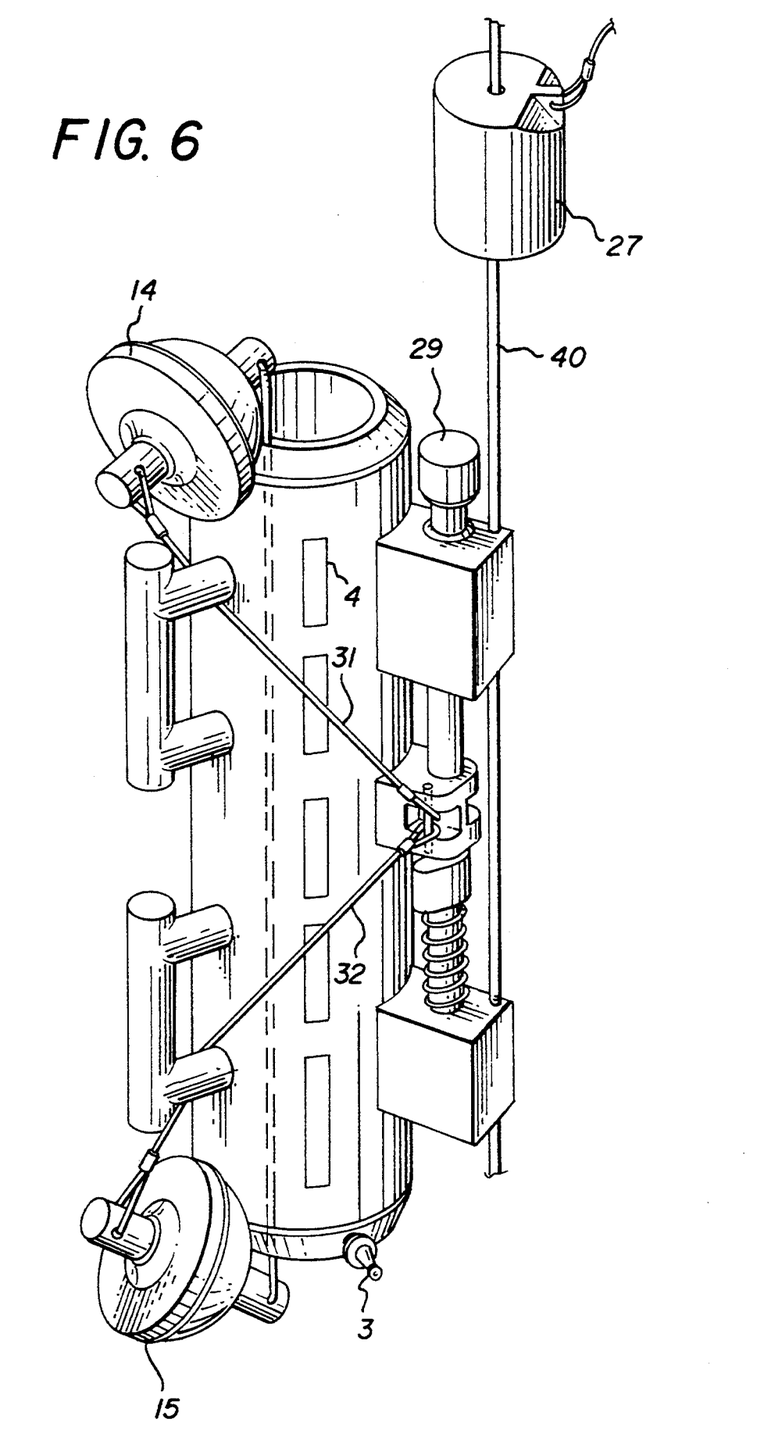
FIG. 6 is a perspective view of the sampler according to the invention.
Figure 7:
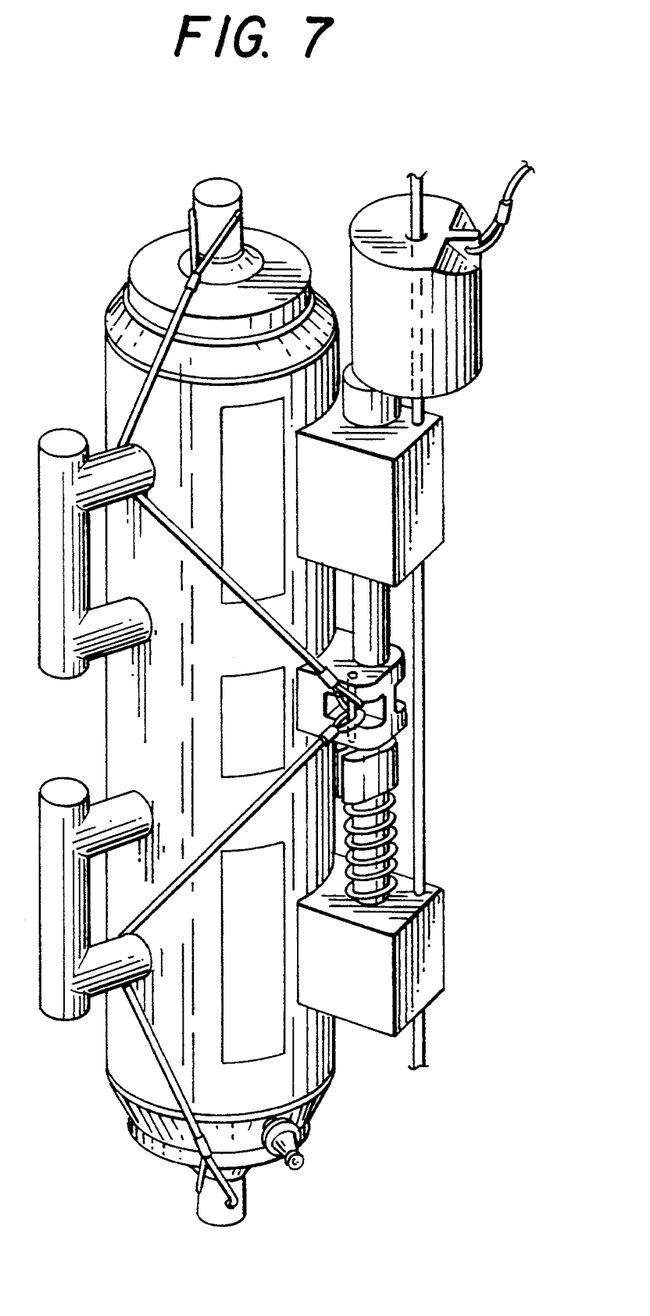
FIG. 7 is a view similar to FIG. 6 of the sampler with closed end plugs and alternatively embodied viewing windows.

FIGS. 6 and 7 show the sampler according to the invention in an open and closed condition, respectively. Viewing windows 4 are strategically distributed on the body of the PVC body to facilitate visual observation of the sample prior to purging the same. Certain contamination, such as sand deposits or oceanic vegetation, may be detected immediately. Various embodiments of windows 4 are possible and only two types are shown in FIGS. 6 and 7, respectively.

The double wall sampler according to the invention is normally mounted on a sampler array or rosette 5 as illustrated in FIG. 2. As shown in FIG. 4, for instance, a hanger 6 is provided on top of the sampler. The hanger 6 is secured to a cable on the mother ship which drops the array into the ocean for sampling. A lower portion or stand 5a of the array 5 permits the unit to stand on the mother ship, or be loaded even prior to being placed on the ship, with the inventive double wall samplers. An upper mount 7 and a lower mount 8 is attached on the outside of the rigid PVC pipe of the sampler. The upper and lower mounts are provided for securing the individual samplers to the sampler array 5.

As mentioned above, one of the main disadvantages of the prior art device is the contamination, i.e. the falsification, of the water sample. The present invention is directed primarily to providing a sampler in which the interior body will be made of inert material, so as to prevent any type of reaction between the sample and the sampler container, as well as prevent any contacting of the water sample with the ambient air during a sample purge.

Figure 8:
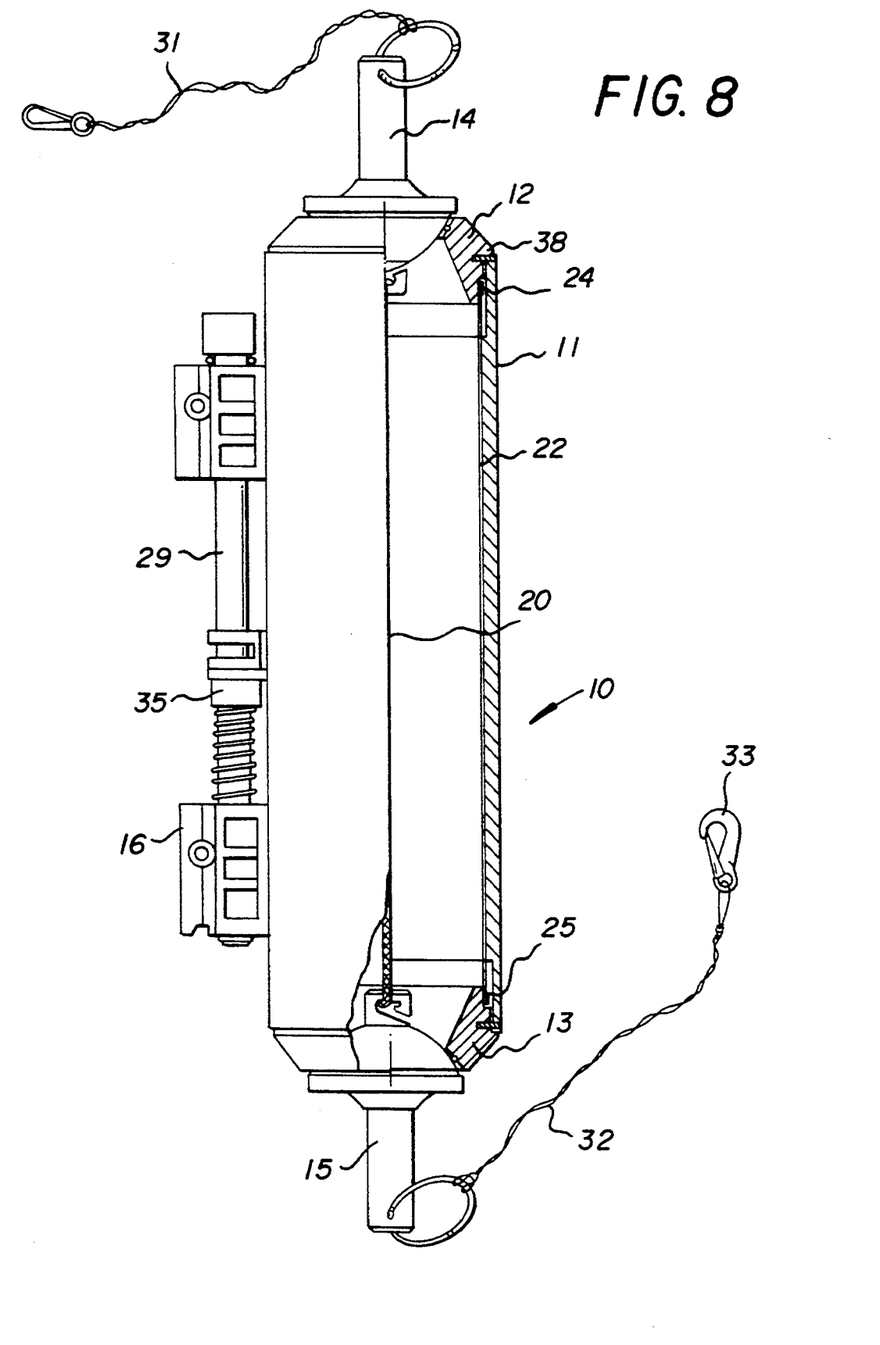
FIG. 8 is a longitudinal, cross-sectional view of the sampler with the flexible liner in its stretched condition.

As seen in FIG. 8, the double wall sampler according to the invention has a hard body 11. The body is shown as being cylindrical in cross-section and tubular in its entire length. Modifications of that basic shape are well within the level of skill of the artisan. It has been found, however, that the most economical and practical shape has been the tubular bodies having a circular cross-section. An upper end portion 12 and a lower end portion 13 are provided at the remote ends of the body 11. The length of the body with the upper and lower end portions is preferably 18 units. Further exemplary dimensions of 13.0, 5.85 and 2.50 units are indicated in FIG. 8. Also an upper end plug 14 and a lower end plug 15 are provided for the upper end portion 12 and the lower end portion 13, respectively. The two end plugs are tied together and pulled one against the other by means of a power spring 20. The power spring 20 can be a rubber spring or a wire spring. Optionally, the spring is wrapped with a liner of polyethylene, or any material of which a flexible liner 22 is made. Both end plugs 14 and 15 are simultaneously secured on the ends of the sampler body to encapsulate and entrap the water sample by the power spring 20. The flexible tubular body 22 is securely attached by collars 24 and 25 to the upper end portion 12 and the lower end portion 13, respectively.

The lower end portion 13 is secured to the rigid PVC body 11 by means of a pin 36, which extends through an opening provided in the body 11 into a bore in the portion 13. A pin 37 shown at the upper end portion 12 is not necessary. In fact the flexible hose-type inner body 22 is resiliently stretched when the end portions 12 and 13 are in place. In other words, when the end portion 13 is attached at the lower end of the rigid tube 11, a stop shoulder 38 prevents the shoulder 12 from slipping into the PVC body 11.

Figures 9, 10:
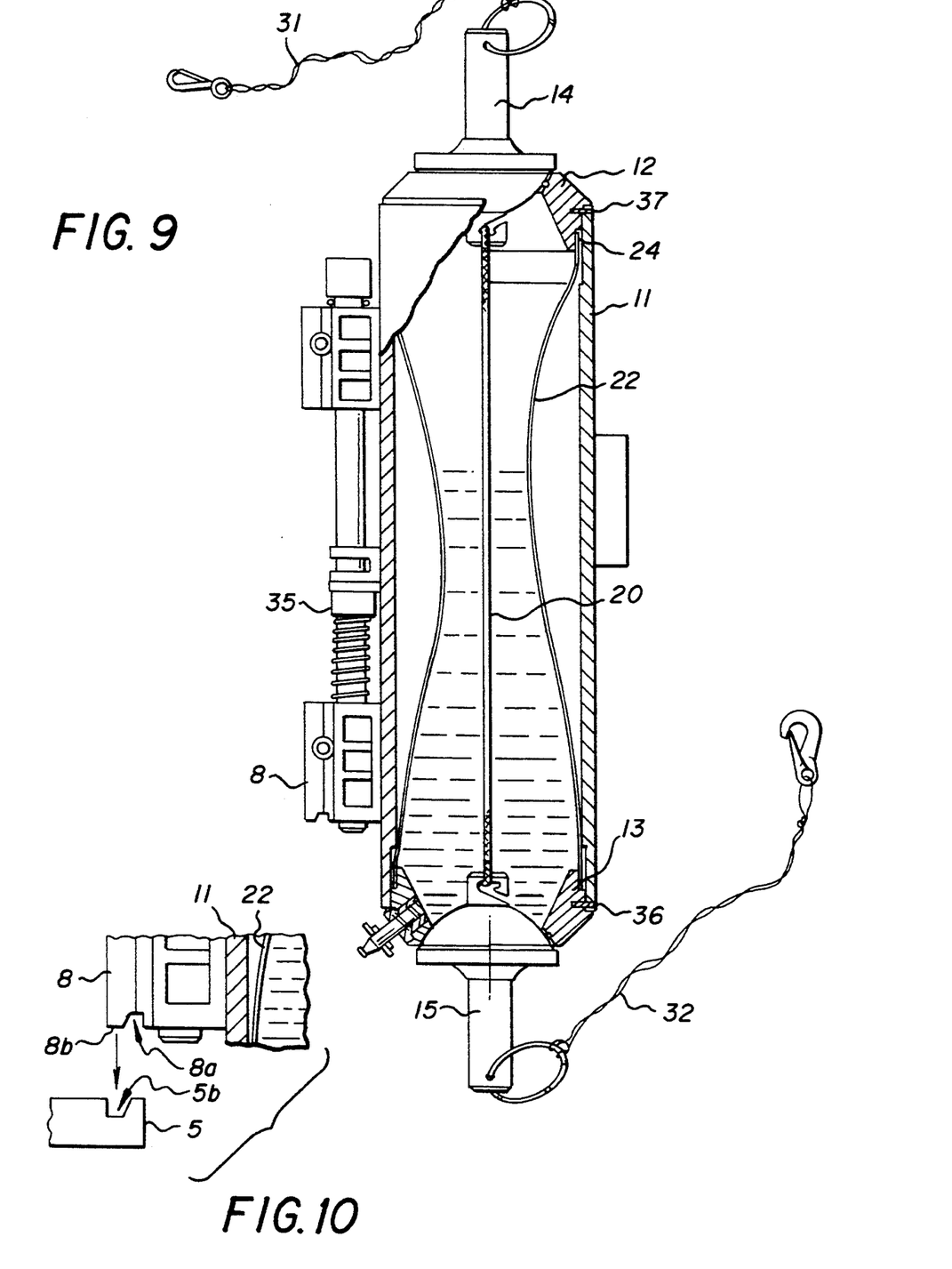
FIG. 9 is a view similar to that of FIG. 8, with the sampler half-filled and the flexible liner partly collapsed.
FIG. 10 is a partial, diagrammatic view of an attachment mechanism by which the sampler according to the invention is placed on a sampler array support.

FIG. 9 shows the interior body 22 slightly deformed when a part of the sample has been purged. Air is thereby allowed to enter into the space between the rigid wall 11 and the flexible wall 22. The collars 12 and 13 are not airtight with respect to the rigid cylinder wall 11. Quite importantly, however, the flexible tubular wall 22 is sealed to the collars 12 and 13, respectively, so as to carefully avoid any contact between the ambient air and the water sample.

When the sampler is to be loaded, the top end plug 14 is pivoted about the upper end edge, then a top lanyard 31 is secured into a release mechanism 35, known from the prior art samplers. Then the lower end plug 15 is pivoted about the lower end edge 13 after which its lower lanyard 32 is securely attached to the top lanyard by its snap 33. The open cocked condition of the sampler is illustrated in FIG. 6. At that point, the double-walled sampler is loaded and ready for sampling. It may be mounted on a wire 40 and secured in place by two wire clamps. After the sampler is lowered into the water and reaches a predetermined depth where a sample is to be taken, a messenger 27 is sent down the support wire 40, it engages the push rod 29, which causes the top lanyard 31 and the lower lanyard 32 is released allowing the power spring 20 to close the upper end plug 14 and lower end plug 15.

Again with reference to FIG. 9, when the water sample is purged, as the water drains from the sampler, the internal flexible body 22 deforms under the atmospheric pressure to compensate for the volume of water drained. This allows for the water sample to drain without opening the air vent to compensate for the change of pressure caused by draining the water. Accordingly, the water is prevented from getting in contact with the atmospheric air and the gases contained in the water sample will not react with the ambient oxygen. Also, the pressure inside the flexible body remains essentially constant during the purging operation with the result that the gases contained in the water sample will not be released. Consequently an accurate evaluation of the water sample is possible.

FIG. 10 shows a portion of the lower mount 8 and a portion of the sampler array rosette 5. The mount 8 is provided with a chamfered groove 8a and thus a chamfered extension 8b, which is placed into and which meshes with a groove 5b provided on the rosette. The oblique surfaces have been found to be extremely advantageous. Firstly, the attachment mechanism is partially self-aligning, in that the oblique surfaces mesh and force exact alignment by way of a conversion of a portion of the vertical force caused by gravity on the sampler into a horizontal force component. Secondly, the sampler can now be tilted as it is placed on the rosette or taken away. In the prior art devices, such tilting often caused the mount 8 to break, leading to costly repairs.

I claim:

1. In a water sampler of the type having a substantially rigid body with two end portions with openings for receiving a water sample, two end plugs for closing the openings, and means for closing the end plugs by remote action so as to entrap a water sample in the substantially rigid body, wherein the improvement comprises:

flexible liner means disposed within the rigid body for receiving the water sample and for preventing direct contact between the water sample and the rigid body, upper collar means disposed between the rigid body and an upper end plug, lower collar means disposed between the rigid body and a lower end plug, said flexible liner means being sealingly attached to said upper and lower collar means, said flexible liner means together with said upper and lower collar means and the upper and lower end plugs defining a sealed container for a water sample.

2. The water sampler according to claim 1, wherein said flexible liner means are formed of a material which is essentially inert relative to water and sodium chloride.

3. The water sampler according to claim 1, wherein said flexible liner means are formed of polyethylene.

4. The water sampler according to claim 1, including valve means disposed in said lower collar means for selectively purging water sample from said sealed container.

5. The water sampler according to claim 1, wherein said upper collar means are disposed between the upper end plug and the rigid body in such a manner as to allow air or water to enter a space defined between said flexible liner means and the rigid body.

* * * * *